United States Patent

Yamada et al.

[11] Patent Number: 6,083,008
[45] Date of Patent: Jul. 4, 2000

[54] OPTICAL PHANTOM OF LIVING BODY AND METHOD FOR PRODUCING IT

[75] Inventors: Yukio Yamada, Tsuchiura; Yukari Tanikawa, Tsukuba; Shuichi Takahashi, Ushiku; Daigo Imai, Oomiya, all of Japan

[73] Assignee: Agency of Industrial Science & Technology, Ministry of International Trade & Industry, Tokyo, Japan

[21] Appl. No.: 09/145,227

[22] Filed: Sep. 1, 1998

[30] Foreign Application Priority Data

Sep. 1, 1997 [JP] Japan .................................. 9-235519

[51] Int. Cl.[7] .................................................. G09B 23/28
[52] U.S. Cl. ............................................ 434/267; 434/268
[58] Field of Search ...................................... 434/262, 267, 434/268, 269, 270, 272

[56] References Cited

U.S. PATENT DOCUMENTS

| | | | |
|---|---|---|---|
| 2,871,579 | 2/1959 | Niiranen et al. | 434/268 |
| 2,995,832 | 8/1961 | Alderson | 434/268 |
| 4,003,141 | 1/1977 | Le Roy | 434/270 |
| 5,055,051 | 10/1991 | Duncan | 434/262 |
| 5,112,228 | 5/1992 | Zouras | 434/267 X |
| 5,518,406 | 5/1996 | Waters | 434/267 |
| 5,620,326 | 4/1997 | Younker | 434/268 |
| 5,727,948 | 3/1998 | Jordan | 434/267 |
| 5,775,916 | 7/1998 | Cooper et al. | 434/267 |
| 5,803,746 | 9/1998 | Barrie et al. | 434/267 |
| 5,839,904 | 11/1998 | Bloom | 434/268 |

FOREIGN PATENT DOCUMENTS 10-222055  8/1998  Japan .

*Primary Examiner*—Sam Rimell
*Attorney, Agent, or Firm*—Oblon, Spivak, McClelland, Maier & Neustadt, P.C.

[57] ABSTRACT

An optical phantom of a living body includes a multiplicity of phantom layers shaped to the contours of a target part of a living body. A space portion is provided at a prescribed location inside the phantom. Inlet and outlet conduits enable liquid phantom to be supplied to the space portion and removed therefrom. This arrangement enables the space portion to be used to simulate dynamic change of physiological states, and for such changes to be measured optically.

4 Claims, 6 Drawing Sheets

OPTICAL PHANTOM OF LIVING BODY AND METHOD FOR PRODUCING IT

BACKGROUND OF THE INVENTION

1. Field of the Invention

This invention relates to an optical phantom of a living body for measuring dynamic changes of physiological states in the course of developing systems for medical diagnosis and treatment, and to a method of producing the optical phantom.

2. Description of the Related Art

In a living body, diseased parts exhibit different light scattering and absorption coefficients compared to normal tissue regions. Technology is therefore being developed that involves irradiating a target examination region with light and measuring the resultant light output to establish the location of diseased tissue regions, diagnose the presence or absence of such a diseased tissue region and treat diseased tissue regions.

However, while in the development of medical diagnostic and treatment equipment that utilizes light, it is important to clarify how the light propagates inside a living body, and which part of the living body is to be diagnosed and treated; this is very difficult to accomplish. If it is possible to produce a phantom that optically simulates the human body and other living bodies, and if the phantom could be internally provided with portions that simulate various diseased parts and tissue functions, it would enable the effectiveness of diagnostic and treatment systems to be accurately evaluated.

Slab-shaped and cylindrical phantoms have been fabricated for basic research. Also, in Japanese Patent Public Disclosure No. 10-222055 the present inventors disclosed an optical phantom simulating the human body. With this phantom, however, it is not possible to optically measure dynamic change in physiological states such as that which takes place in muscles, the brain, and blood flow.

An object of the present invention is to provide an optical phantom that enables dynamic changes in physiological state to be measured, and a method for producing the optical phantom.

SUMMARY OF THE INVENTION

For achieving this object, the present invention provides an optical phantom of a target portion of a living body, the phantom being formed in a shape of the target portion and comprising a plurality of stacked phantom layers of resin, with the resin of each phantom layer adjusted to have optical properties of a corresponding target portion, a space portion provided inside the phantom, an inlet conduit provided in the phantom with one end opening into the space portion and another end opening to outside the phantom, and an outlet conduit provided in the phantom with one end opening into the space portion and another end opening to outside the phantom.

The present invention also provides a method of producing an optical phantom of a living body, by providing a base with a conduit material, forming on a surface of the base at least one phantom layer using a female mold in a shape of a target part of the living body, with said phantom layer embedding the conduit material, providing a spacing material at a prescribed position on the phantom layer where the spacing material is in contact with the conduit material, forming another phantom layer on an outer side of the phantom layer that includes the spacing material, using another female mold in a shape of the target part of the living body, removing the conduit material from the phantom to thereby constitute an inlet conduit and an outlet conduit, and using the conduits to remove the spacing material portion to thereby form a space portion.

Thus, in accordance with the present invention, there is provided an optical phantom of a living body portion comprised of a plurality of phantom layers formed of resin adjusted to have the optical properties of the target portion, and a space portion is provided at a prescribed location inside the phantom. By supplying the space portion with specific liquid phantoms, it is possible to dynamically simulate functional and diseased parts. Thus, how light is propagated and optical changes inside the living body can be revealed by measuring the states of such parts. As such, the present invention provides a way of precisely evaluating the effectiveness of diagnostic and treatment systems, and can also be used in diagnoses and treatments for a living body.

The above and other features of the present invention will become apparent from the following description made with reference to the drawings.

DESCRIPTION OF THE PREFERRED EMBODIMENT

Figure 1:
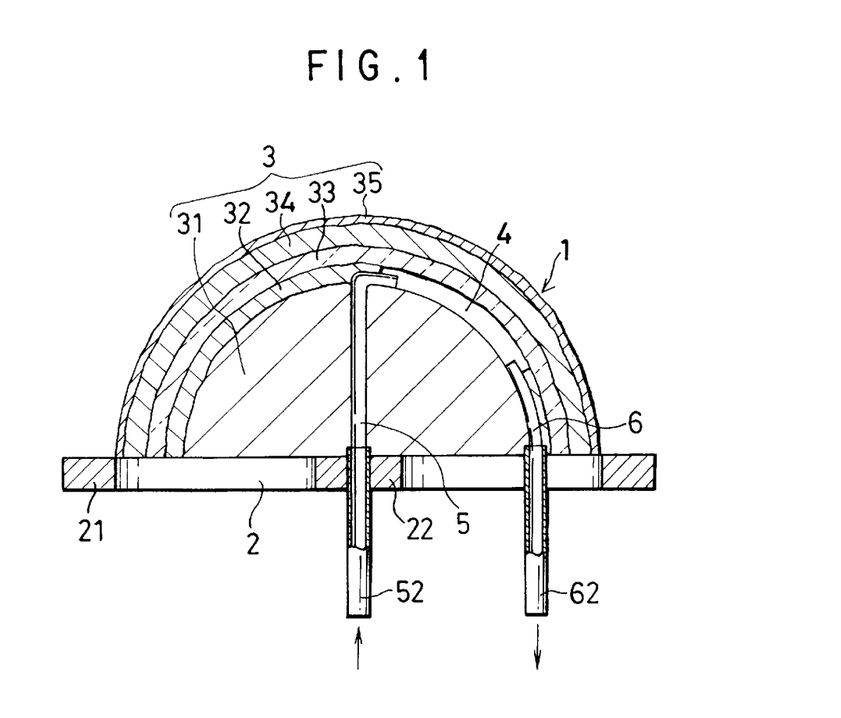
FIG. 1 is a cross-sectional view of an optical phantom of a living body for simulating a human head, in accordance with an embodiment of the present invention.

FIG. 1 shows an optical phantom 1 simulating a human head according to an embodiment of the present invention. With reference to the drawing, the optical phantom 1 comprises a base 2, a plurality of phantom layers 3 stacked on the surface of the base 2, some of the phantom layers 3 being provided with a space portion 4. The optical phantom 1 also has an inlet conduit 5 and an outlet conduit 6, with each of the conduits communicating with the space portion 4 and opening to the outside of the phantom.

In the illustrated embodiment, the base 2 comprises a ring 21 and a cross-shaped reinforcement portion 22 and is formed of synthetic resin. It is to be understood that the base 2 may be constituted of another material and be configured differently.

The phantom layers 3 stacked on the base 2 comprise five phantom layers 31 to 35. The innermost layer, first phantom layer 31, simulates white matter, the next layer, second phantom layer 32, simulates grey matter, third phantom layer 33 simulates cerebrospinal fluid, fourth phantom layer 34 simulates a skull, and the outermost layer, fifth phantom layer 35, simulates the skin covering the skull.

Titanium oxide particles, ink, dye and the like were added to the epoxy resin or polyester resin base material of the phantom layers 31 to 35 to impart to the layers the different optical properties specific for each of the layers representing the respective parts of the head. The feel of skin can be obtained by using a flexible resin such as silicone rubber to form the fifth phantom layer 35.

At least one of the phantom layers 31 to 35 is provided with a space portion 4 at a location where it can simulate functional parts of physiological tissue activity or diseased parts, and the inlet and outlet conduits 5 and 6 simulating blood vessels that connect the space portion 4 to the outside of the head phantom. By selecting a phantom liquid that simulates a diseased portion or physiological tissue activity and using an external circulation system (not shown) to circulate the liquid through the space portion 4 via the inlet conduit 5 and outlet conduit 6, it is possible to simulate changes in blood flow accompanying muscle and brain activity, and to simulate other liquids, thereby making it possible to optically measure dynamic changes of physiological states simulated within the phantom.

Thus, by providing the optical phantom 1 with space portions in accordance with the present invention, it is possible to simulate a diseased portion or dynamic portion taking place at a part of a living human or animal body. In addition, it is also possible to use the flow of phantom liquid into the space portion 4 to simulate and optically measure dynamic changes of physiological states such as, for example, blood flow changes, changes in oxygen flow in tissues and changes in cellular sugar content.

The method of producing the optical phantom 1 of this invention will now be described, based on the arrangement of the embodiment shown in FIG. 2.

As the above optical phantom 1 was described with reference to the simulation of a human head, the explanation of the method of producing the phantom will also be made with reference to a head phantom.

The optical phantom 1 was modeled on data compiled from multiple sectional anatomical images of the head acquired using an apparatus able to collect three-dimensional shapes such as an MRI or X-ray CT system. The model data were then fed to an image contouring apparatus to fabricate prototypes of each section in photo-polymerizing resin or the like, which were then used to fabricate female molds of silicone rubber.

Figure 2A:
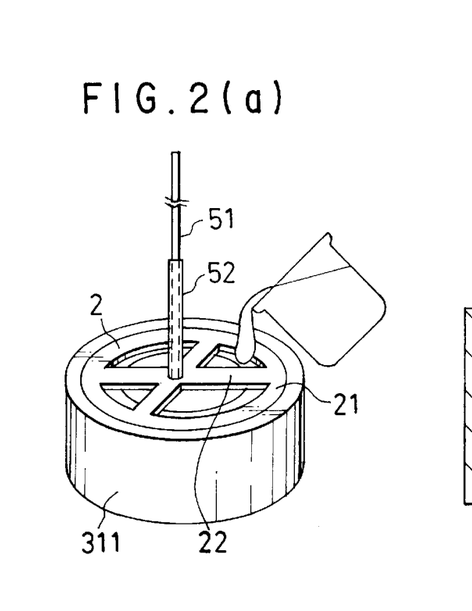
FIG. 2(a) is a perspective view of the fabrication of a first phantom layer of the optical phantom of FIG. 1.
Figure 2B:
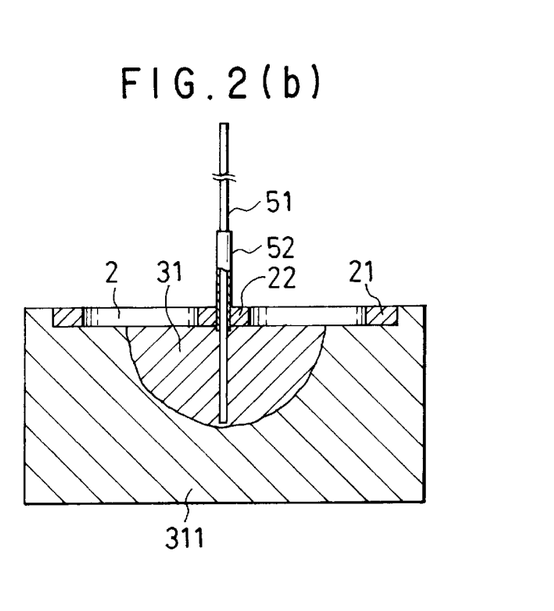
FIG. 2(b) is a cross-sectional view of the arrangement shown in FIG. 2(a).
Figure 5A:
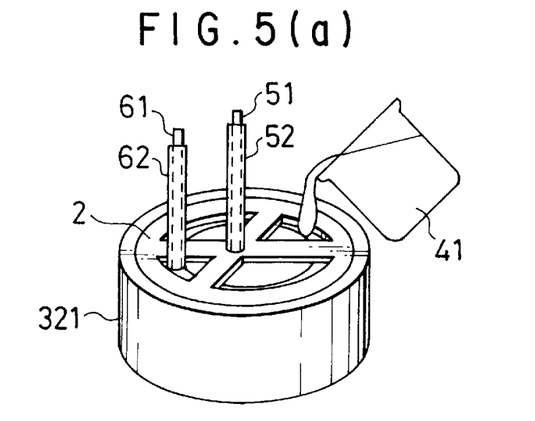
FIG. 5(a) is a perspective view illustrating the formation of a space layer by the material for spaces on the outer surface of the first phantom layer of FIG. 4(c).
Figure 5B:
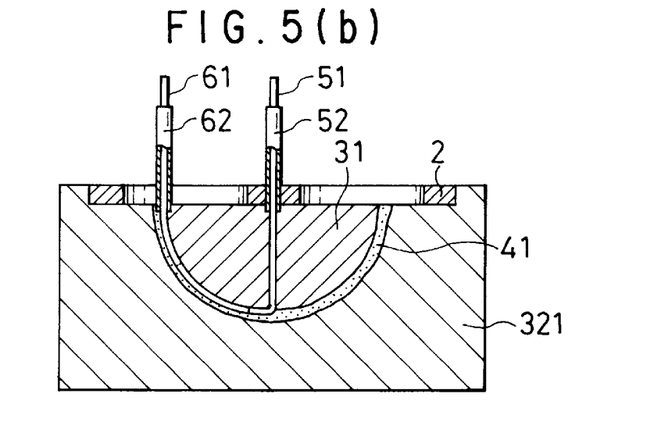
FIG. 5(b) is a cross-sectional view of the arrangement shown in FIG. 5(a).
Figures 7A, 7B, 7C:
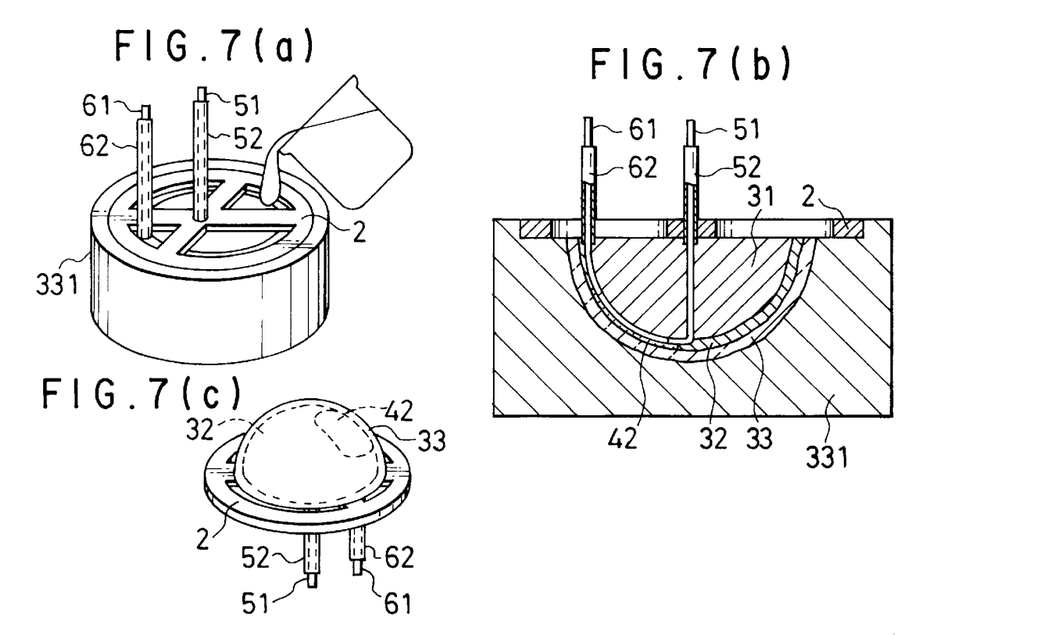
FIG. 7(a) is a perspective view illustrating the forming of a third phantom layer on the surface of the second phantom layer of FIG. 6(c).
FIG. 7(b) is a cross-sectional view of the arrangement shown in FIG. 7(a).
FIG. 7(c) is a perspective view illustrating the formation of the third phantom layer.
Figures 10A, 10B, 10C:
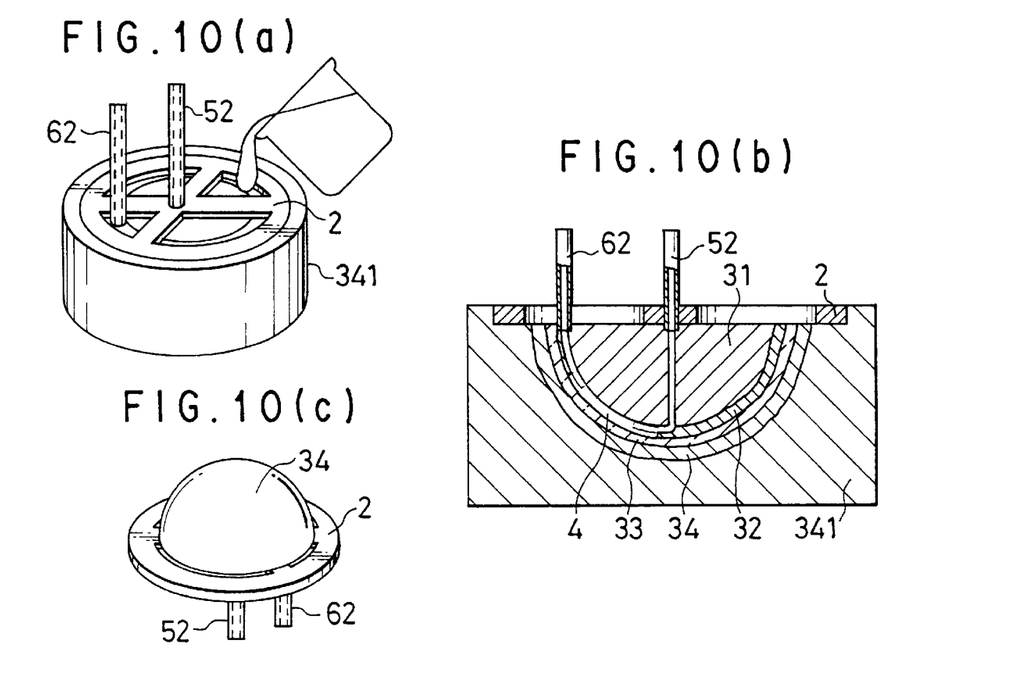
FIG. 10(a) is a perspective view illustrating the formation of a fourth phantom layer on the space portion of FIG. 9(b).
FIG. 10(b) is a cross-sectional view of the arrangement shown in FIG. 10(a).
FIG. 10(c) is a perspective view illustrating the formation of the fourth phantom layer.
Figures 11A, 11B, 11C:
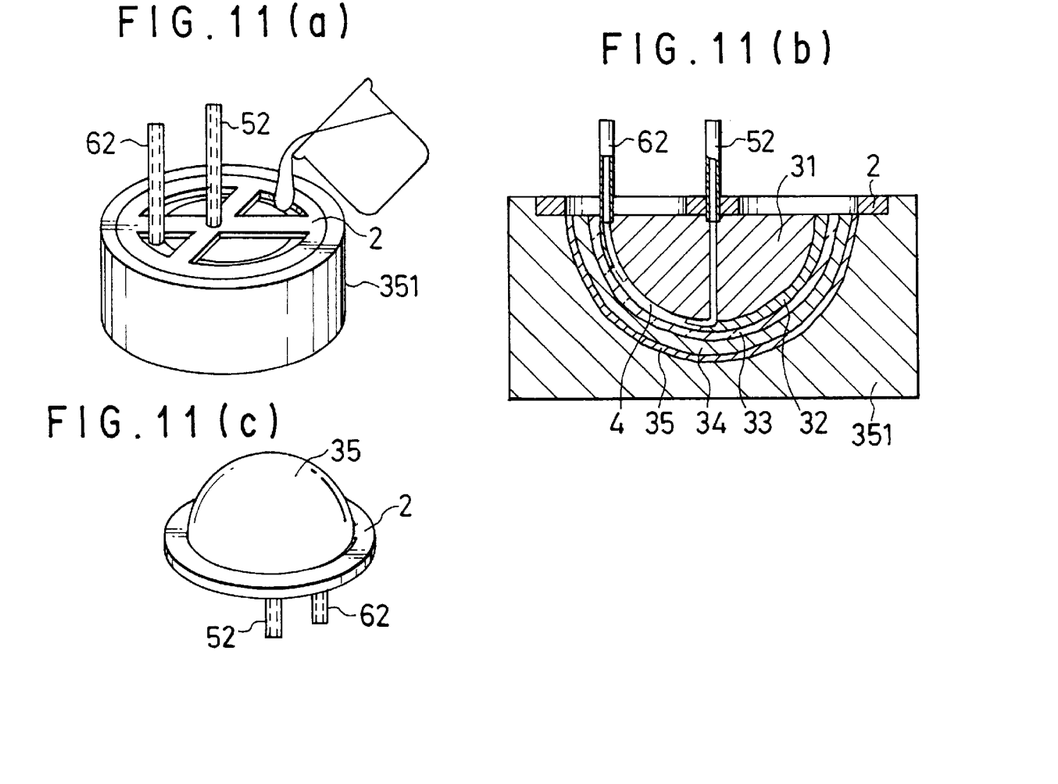
FIG. 11(a) is a perspective view illustrating the formation of a fifth phantom layer on the surface of the fourth phantom layer of FIG. 10(c).
FIG. 11(b) is a cross-sectional view of the arrangement shown in FIG. 11(a).
FIG. 11(c) is a perspective view illustrating the formation of the fifth phantom layer.

In this way, first, second, third, fourth and fifth silicone rubber female molds 311 (FIG. 2(b)), 321 (FIG. 5(b)), 331 (FIG. 7(b)), 341 (FIG. 10(b)) and 351 (FIG. 11(b)) were prepared for the phantom layers 31 to 35 of the optical phantom of FIG. 1.

In FIGS. 2(a) and 2(b), first conduit material 51 is inserted through the center part of the base 2 to form the inlet conduit. The first conduit material 51 was fitted with a liquid phantom inlet tube 52 down onto the opening of the first female mold 311 used to form the external shape of the first phantom layer 31. Then, via an opening of the base 2, the opening of the first female mold 311 is charged with epoxy resin, polyester resin or other such casting material adjusted to exhibit the required optical properties by the addition of titanium oxide particles, ink, dye and the like.

Figure 3:
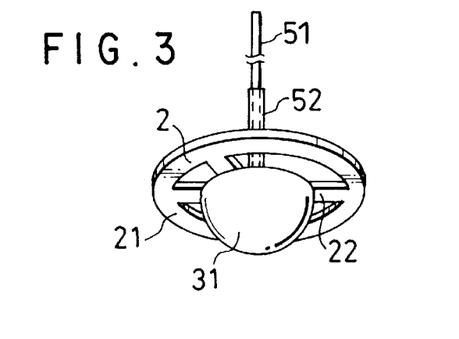
FIG. 3 is a perspective view illustrating the forming of the first phantom layer on the base.

After the material is cast into the first female mold 311 and is solidified, it is removed from the mold. In this way, as seen in FIG. 3, a first phantom layer 31 having the same shape as the inside contour of the first female mold is formed on the base 2.

The first conduit material 51 can be formed as a hollow bar or a tubular member of a material such as Teflon resin that can be bent and does not adhere to the epoxy or polyester resin of the phantom layer. Similarly, the inlet tube 52 can be formed as a tubular member of a plastic such as, for example, vinyl material that does adhere to the epoxy or polyester resin.

Figure 4A:
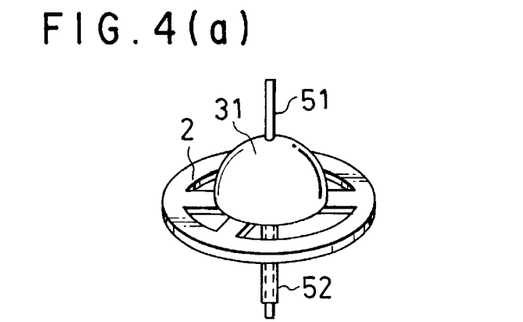
FIG. 4(a) is a perspective view showing the material of a first conduit projecting from the surface of the first phantom layer of FIG. 3.

When the first phantom layer 31 is thus formed in FIG. 4(a) on the base 2 by the removal of the first female mold, the first conduit material 51 is pushed until the tip of the first conduit material 51 projects from the outside surface of the first phantom layer 31.

Figure 4B:
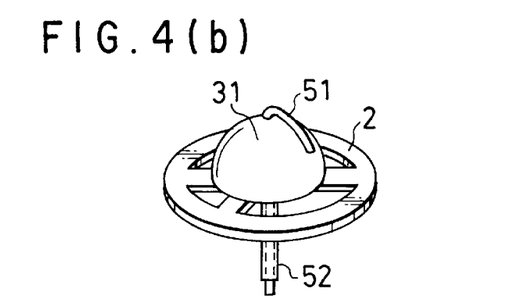
FIG. 4(b) is a perspective view showing the first conduit bent along the outer surface of the first phantom layer.

The projecting end of the first conduit material 51 is then bent in contact on the surface of the first phantom layer 31 (FIG. 4(b)). Next, to form the outlet conduit in FIG. 4(c) a second conduit material 61 is arranged along the surface of the first phantom layer 31, so that the end portions of the first conduit material 51 and the second conduit material 61 are affixed in contact on the surface of the first phantom layer 31.

Figure 4C:
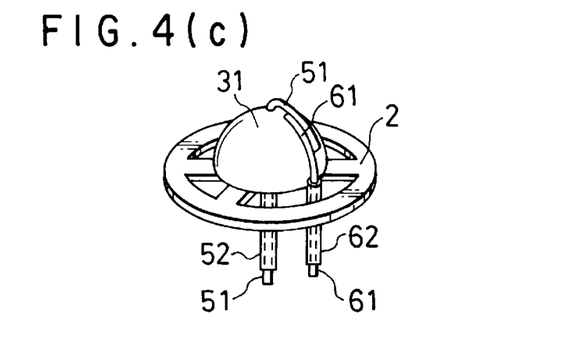
FIG. 4(c) is a perspective view showing a second conduit provided on the outer surface of the first phantom layer.

A liquid phantom outlet tube 62 is fitted to the second conduit material 61. As in the case of the first conduit material 51, the second conduit material 61 is formed of a plastic that does not adhere to the first phantom layer 31, while the outlet tube 62 is formed of a plastic that does adhere to the first phantom layer 31.

Figure 5C:
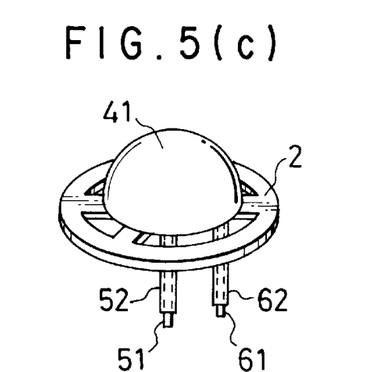
FIG. 5(c) is a perspective view of the first phantom layer of FIG. 5(a) taken out of the mold.

When the first conduit material 51 and second conduit material 61 have been arranged on the surface of the first phantom layer 31 with the ends thereof overlapping, the first phantom layer is fitted into the inside of the second female mold 321 in FIG. 5(a), through the opening thereof, that forms the outside shape of the second phantom layer. Spacing material 41 is then injected into the space formed between the outer surface of the first phantom layer and the inner surface of the second female mold 321, and is solidified. The first phantom layer 31 is in FIG. 5(b) is then removed from the mold 321, leaving spacing material 41 just at the position where the space portion is thereby constituted. Other parts of the spacing material 41 in FIG. 5(c) are cut off and removed, leaving the remaining portion of the spacing material 41 to form a spacing material portion 42 (FIG. 5). This step results in a configuration in which the ends of the first conduit material 51 and second conduit material 61 are embedded in the spacing material portion 42.

As the spacing material 41, there may be used a material that at normal temperatures can maintain its shape to a certain degree, but readily liquifies when heated, such as agar, gelatin or paraffin, or a material such as sodium hydroxide that is readily liquified by chemical means. Similarly sugar or paper clay, which also readily dissolve in water, can be used for this purpose, too.

Figure 5D:
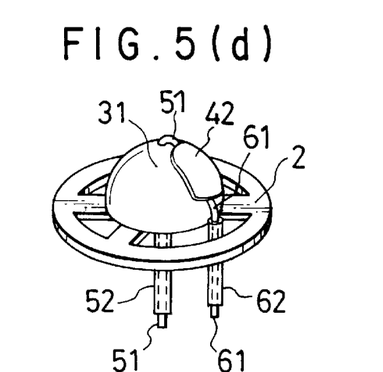
FIG. 5(d) is a perspective view showing the material for spaces left at just the prescribed places on the first phantom layer of FIG. 5(c).

Thus, as shown in FIG. 5(d), the spacing material portion 42 is provided on the outside of the first phantom layer 31 in communication with the ends of the first conduit material 51 and second conduit material 61.

Figure 6A:
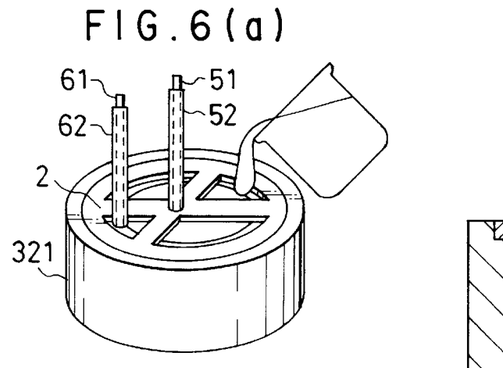
FIG. 6(a) is a perspective view illustrating the forming of a second phantom layer on the surface of the first phantom layer of FIG. 5(d).
Figure 6B:
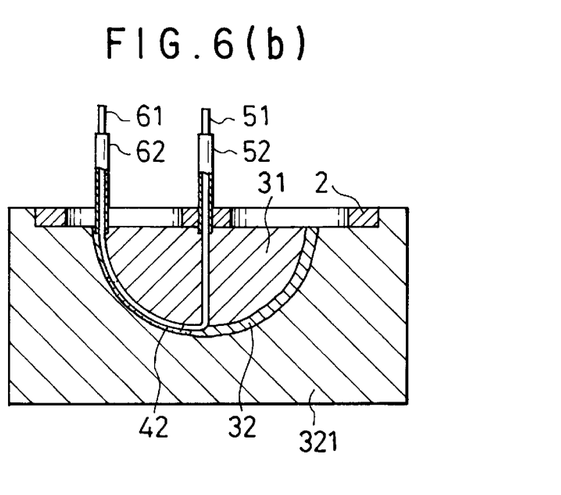
FIG. 6(b) is a cross-sectional view of the arrangement shown in FIG. 6(a).

The first phantom layer provided with the spacing material portion is again placed in the interior of the second female mold 321 in FIG. 6(a) through the opening thereof and the second phantom layer 32 is formed in FIG. 6(b) in the space between the outer surface of the first phantom layer 31 and the inner surface of the second female mold 321 by the insertion of epoxy or polyester resin in which is mixed titanium oxide particles, ink, dye and the like to adjust the optical properties of the material. Once the material has been solidified, it is removed from the mold (FIG. 6(c)).

Figure 6C:
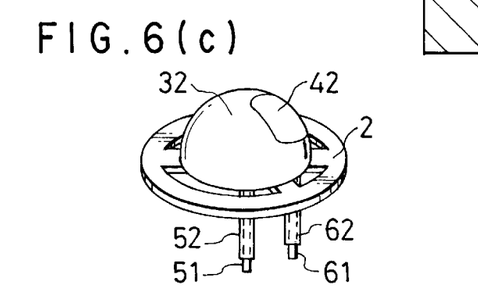
FIG. 6(c) is a perspective view illustrating the formation of the second phantom layer.

In this way, part of the spacing material portion 42 is exposed on the surface of the first phantom layer, while the remaining exposed portion forms the second phantom layer 32 (FIG. 6(c)).

The phantom now comprised of the first phantom layer and second phantom layer on the base 2 is inserted into the opening of the third female mold 331 in FIG. 7(a) used to form the third phantom layer 33, which is formed in FIG. 7(b) in the space between the inner surface of the third female mold 331 and the outer surface of the second phantom layer 32 by the insertion of epoxy or polyester resin in which is mixed titanium oxide particles, ink, dye and the like to adjust the optical properties of the material. Once the material has been solidified, it is removed from the mold (FIG. 7(c)).

In this way, the third phantom layer 33 is formed on the outer surface of the second phantom layer 32 provided with the spacing material portion 42, thus forming on the base 2 a phantom comprised of three layers (FIG. 7(c)).

Figure 8A:
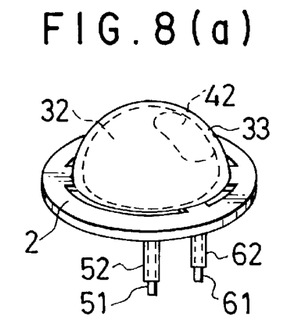
FIG. 8(a) is a perspective view illustrating the formation of the third phantom layer.
Figure 8B:
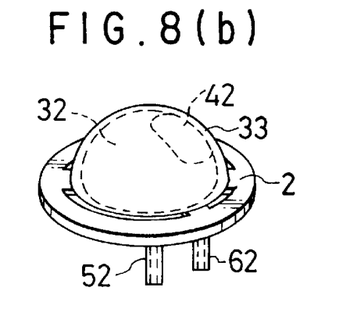
FIG. 8(b) is a perspective view of the phantom of FIG. 8(a) from which the first and second conduit materials (tubes) have been removed.

When the three-layer phantom has thus been formed, the inlet conduit to the space portion and the outlet conduit are formed between the first phantom layer and the second phantom layer 32 in FIG. 8(a) by withdrawing the first conduit material 51 and second conduit material 61, also forming the inlet tube 52 and the outlet tube 62 at the ends of the inlet conduit and outlet conduit (FIG. 8(b)).

Figure 8C:
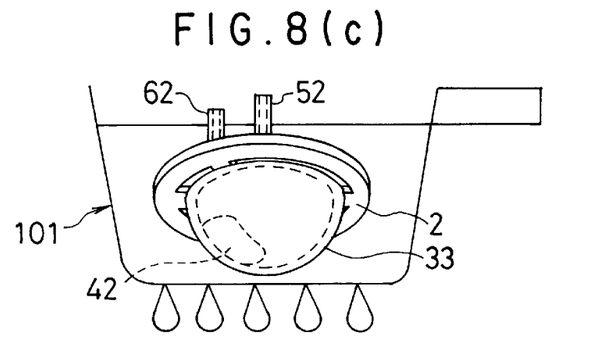
FIG. 8(c) is a perspective view showing the phantom of FIG. 8(b) being heated.

In this state, a heater 101 is then used to apply enough heat to liquify the spacing material portion 42 without altering the qualities of the materials of the first phantom layer, second phantom layer and third phantom layer 33 (FIG. 8(c)).

If the spacing material is one that is readily decomposed to be liquified by a chemical agent, the chemical agent is injected via the inlet tube 52 to dissolve the spacing material portion 42. The chemical agent used is one that does not react with the epoxy or polyester resin used to constitute the first phantom layer, second phantom layer and third phantom layer 33.

Figure 9A:
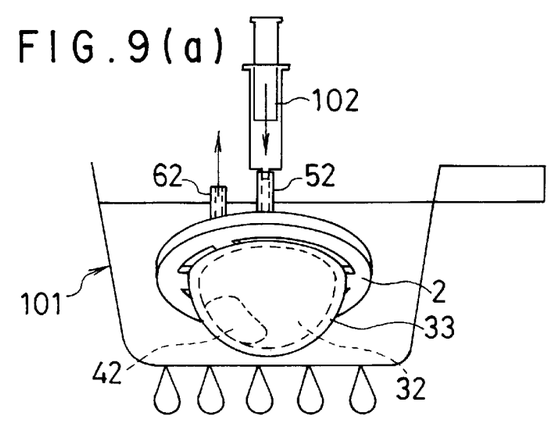
FIG. 9(a) is a perspective view illustrating the removal of space material from the heated phantom of FIG. 8(c).

Once the spacing material portion 42 is thus liquefied, a pressure application structure 102 shown in FIG. 9(a) is connected to the inlet tube 52 to feed air or warm water under pressure into the liquified spacing material portion 42 to thereby flush the spacing material portion 42 out through the outlet tube 62. The third phantom layer 33 can be formed as a transparent layer and the spacing material portion 42 given a different color from the second phantom layer 32 to make it possible to visually confirm the flushing out of the spacing material portion 42 through the third phantom layer 33. The flushing out of the spacing material portion 42 results in the formation of the space portion on the second phantom layer 32, sandwiched between the outer surface of the first phantom layer and the inner surface of the third phantom layer 33.

Figure 9B:
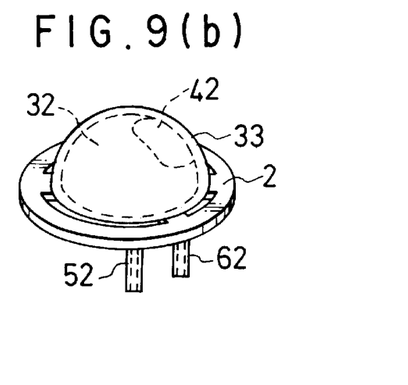
FIG. 9(b) is a perspective view illustrating space formation by removal of material from the phantom of FIG. 9(a).

A phantom comprising the first phantom layer, the second phantom layer 32 with the space portion and the third phantom layer 33 on the base 2 is thus formed (FIG. 9(b)).

The three-layer phantom is then inserted into the fourth female mold 341 in FIG. 10(a) to form the fourth phantom layer 34 in FIG. 10(b), which is formed in the space between the inner surface of the fourth female mold 341 and the outer surface of the third phantom layer 33 by the insertion of epoxy or polyester resin in which is mixed titanium oxide particles, ink, dye and the like to adjust the optical properties of the material. Once the material has been solidified, it can be removed from the mold as what is now a four-layer phantom comprised of first to fourth phantom layers 34 (FIG. 10(c)).

The four-layer phantom is then inserted into the fifth female mold 351 in FIG. 11(a) used to form the fifth phantom layer 35, which is formed in FIG. 11(b) by resin inserted into the space between the inner surface of the fifth female mold 351 and the outer surface of the fourth phantom layer 34. In this embodiment the fifth phantom layer 35 simulates the skin of the head, for which a resin may be used that is adjusted to the required optical properties and flexible and skin-like to the touch, such as, for example, silicone rubber. Once the fifth phantom layer 35 has been solidified, the phantom can be removed from the mold. In this way, a phantom can be obtained that uses the composition of the five phantom layers to simulate a head (FIG. 11(c)).

The above method enables the optical phantom 1 of FIG. 1 to be fabricated of phantom layers 31–35 each having specific optical properties and that is also provided with the internal space portion 4 to which phantom liquid can be supplied via inlet conduit 5 and drained out via outlet conduit 6.

The phantom layers 31–35 can be formed in the atmosphere, but are formed in a vacuum in cases where the formed phantom layers may otherwise contain air bubbles.

While the present invention has been explained in the foregoing description with reference to the drawings, the invention is not limited to the described embodiments. It is therefore to be understood that within the scope of the appended claims, the invention may be practiced otherwise than as specifically described herein. For example, the phantoms are not limited to the human body, but may be those simulating all parts of animals. Moreover, a full range of physiological and pathological states may be simulated by using, as the phantom liquid flowing to space portions, fluids that simulate blood flow, or fluids that simulate oxygen changes in tissue, or changes of sugar content in cells. Similarly, the number of phantom layers is not limited to the five layers described with reference to the above embodiment, and spaces may be provided in any layer, and at any location, and in any number.

Furthermore, the inlet and outlet conduits do not have to be integrally formed as described above, but may be in the form of pipes attached after the phantom has been formed, using a bonding agent or threaded fasteners or the like.

As described, the phantom in accordance with this invention is comprised of multiple phantom layers in the shape of a target region, with at least one of the phantom layers being provided with a space portion, to which inlet and outlet conduits are connected to enable liquid phantom to flow into and out of the space portion. This arrangement enables dynamic change of physiological states to be optically simulated and measured.

Thus, functional and diseased parts of a living human or animal body may be simulated in the space portions, and changes in blood flow, in oxygen flows in tissue and in cellular sugar levels can be simulated by supplying specific liquid phantoms to the space portions, making it possible to optically measure simulated dynamic change of physiological states. In the development of diagnostic and treatment systems, this device makes it possible to clarify just how light is propagated in the living body, and to diagnose and treat specific parts of the living body, and as such provides a way of accurately, highly and precisely evaluating the effectiveness of such diagnostic and treatment systems, thus making a notable contribution to the fields of the diagnosis and treatment of the living body.

A female mold is used to form at least one phantom layer on the base, provide a spacing material portion in the phantom layer and remove the spacing material portion to thereby fabricate an optical phantom having a space portion formed therein. Thus, it is possible to readily form phantoms of any type, meaning that the invention has a high utility value, especially in the areas of medical diagnosis and treatment.

What is claimed is:

1. A method of producing an optical phantom of a living body, comprising:

providing a base with a conduit material, forming on a surface of the base at least one phantom layer using a female mold in a shape of a target part of the living body, with said phantom layer embedding the conduit material, providing a spacing material at a prescribed position on the phantom layer where the spacing material is in contact with the conduit material, forming another phantom layer on an outer side of the phantom layer that includes the spacing material, using another female mold in a shape of the target part of the living body, removing the conduit material from the phantom to thereby constitute an inlet conduit and an outlet conduit, and using said conduits to remove the spacing material to thereby form a space portion.

2. The method of producing a phantom according to claim 1, wherein the phantom layers constituting the phantom are each comprised of resin having optical properties corresponding to optical properties of the target part of the living body.

3. The method of producing a phantom according to claim 2, wherein the conduit material is a material that does not adhere to the resin.

4. The method of producing a phantom according to claim 1, wherein the spacing material is comprised of a material that liquefies when heated.

* * * * *